United States Patent
Lichtman et al.

[19]

[11] Patent Number: 5,935,057
[45] Date of Patent: Aug. 10, 1999

[54] DEVICE FOR CARRYING TWO UNITS IN END TO END DISPOSITION AND FOR MOVING ONE OF THE UNITS ALONGSIDE THE OTHER OF THE UNITS

[75] Inventors: Philip R. Lichtman, Newton; Koichiro Hori, Framingham, both of Mass.

[73] Assignee: Vista Medical Technologies, Inc., Carlsbad, Calif.

[21] Appl. No.: 09/058,674

[22] Filed: Apr. 10, 1998

Related U.S. Application Data

[63] Continuation-in-part of application No. 08/628,448, Apr. 5, 1996, Pat. No. 5,782,752.

[51] Int. Cl.$^6$ .............................. A61B 1/05; F16H 21/50
[52] U.S. Cl. ..................... 600/137; 600/129; 600/173; 74/22 A
[58] Field of Search ................... 600/101, 106, 600/109, 112, 129, 137, 166, 173; 74/89.17, 89.13, 89.15, 22 R, 22 A

[56] References Cited

U.S. PATENT DOCUMENTS

| | | | |
|---|---|---|---|
| 5,025,778 | 6/1991 | Silverstein et al. | 600/109 X |
| 5,166,787 | 11/1992 | Irion | 348/76 |
| 5,305,121 | 4/1994 | Moll | 348/65 X |
| 5,538,497 | 7/1996 | Hori | 600/137 X |
| 5,653,677 | 8/1997 | Okada et al. | 600/111 |

*Primary Examiner*—John P. Leubecker
*Attorney, Agent, or Firm*—Pandiscio & Pandiscio

[57] ABSTRACT

A device carries first and second units in aligned end-to-end disposition at a distal end of a shaft and provides structure for moving the second of the units into position alongside the first of the units. The device comprises a base portion to which a proximal end of the shaft is fixed, the first unit being fixed to a distal end of the shaft. A rod extends lengthwise through the shaft and a portion of the first unit, and is off-set from an axis of the shaft and fixed to the second unit removed from an axis of the second unit. Mounted on the base portion is an operating mechanism for effecting rotational movement of the rod to effect rotational movement of the second unit to a position removed from alignment with the first unit, and for effecting axial movement of the rod to effect axial movement of the second unit into the position alongside the first unit, said operating mechanism comprising a gear clutch mechanism for shifting movement of said rod from a rotational mode to an axial translational mode, and back again to said rotational mode.

22 Claims, 4 Drawing Sheets

DEVICE FOR CARRYING TWO UNITS IN END TO END DISPOSITION AND FOR MOVING ONE OF THE UNITS ALONGSIDE THE OTHER OF THE UNITS

CROSS-REFERENCE TO RELATED APPLICATION

This is a continuation-in-part of patent application Ser. No. 08/628,448, filed Apr. 5, 1996, in the name of Philip R. Lichtman now U.S. Pat. No. 5,782,752.

BACKGROUND OF THE INVENTION

1. Field of the Invention

The invention relates to mechanical devices for carrying a plurality of units in a first disposition and moving at least one of the units to a second disposition relative to at least one other of the units, and is directed more particularly to a device for supporting and carrying two units end-to-end and for moving one of the units alongside the other of the units.

2. Description of the Prior Art

There are instances in which it is desired to mount and carry units in tandem for passing the units through as small an orifice as possible in a boundary layer and then rearranging the units in a side-by-side relationship.

In the field of medical instruments, for example, it is beneficial in endoscopic examination and surgery to introduce two or more units serially through a relatively small orifice and, once inside the body, reposition the units side-by-side, a disposition of units which, if inserted initially, would require an orifice twice as large, or more, than the small orifice required for introduction of the units in tandem.

In endoscopes, it is known to provide an electronic optical image sensor (hereinafter also referred to as a video device or camera) at the distal end of the endoscope shaft. Such video devices are shown and described in the following U.S. Pat. Nos. 4,832,003, issued May 23, 1989, in the name of Hisao Yabe; 5,021,888, issued Jun. 4, 1991, in the name of Yuu Kondau, et al; 5,166,787, issued Nov. 24, 1992, in the name of Keaus Ission; 5,662,584, issued Sep. 2, 1997 in the name of Koichiro Hori et al., and 5,538,497, issued Jul. 23, 1996 in the name of Koichiro Hori. In the field of endoscopes, it would be beneficial to provide an endoscope shaft with two or more electronic optical image sensors which could be introduced into the body serially and, once inside the body, rearranged to side-by-side positions, such that two or more images could be transmitted to provide to an operator a stereoscopic view of the body portion under examination.

In surgery, it is desirable to limit the size of an incision required for introduction of surgical tools and for viewing of the area of concern. It would be beneficial to have available an instrument by which two units could be introduced serially through an orifice of limited size, with one of the units carrying the required tool and the other unit movable to a position alongside the first unit and carrying image sensing means for providing a view of the tool in operation.

Such an instrument could prove beneficial in any application or area of use wherein it is desired to limit the size of an orifice through a boundary layer, to pass two or more units through the orifice and, thereafter, to position the units side-by-side. Thus, for example, it is desired and often necessary to severely limit the size of any orifice in the pressure hull of deep underwater vehicles. It is also desirable to use acoustics sensors on such vehicles for determining range, with at least two sensors being required for purposes of triangulation and thereby determination of range. It is recognized that a device adapted to pass acoustic sensors through a pressure hull serially and thereafter position the sensors side-by-side would be beneficial in underwater detection and tracking assemblies.

SUMMARY OF THE INVENTION

An object of the invention is to provide a novel device for supporting and carrying two units end-to-end such that the units may be passed through a relatively small orifice in a boundary layer and, thereafter, positioned side-by-side.

A further object of the invention is to provide such a device having novel means for rotatively moving one of the two units out of axial alignment with the other of the units and, thereafter, axially moving the one unit relative the other unit.

A still further object of the invention is to provide an endoscope for supporting and carrying two units, at least one of which is an electronic optical image sensor, end-to-end such that the units may be passed through a relatively small orifice in a mammal body and, thereafter, for positioning the units side-by-side.

A still further object of the invention is to provide a novel drive assembly for imparting rotative and axial movement to a rod affixed to one of the aforementioned units, whereby to effect rotational and axial movement of one unit relative to the other of the units.

With the above and other objects in view, as will hereinafter appear, a feature of the present invention is the provision of a device for carrying first and second units in aligned end-to-end disposition at the distal end of a shaft and for moving one of the units into position alongside the other of the units. The device comprises a base portion to which a proximal end of the shaft is fixed. A first unit of the two is fixed to the distal end of the shaft and is in alignment with the shaft. A rod extends lengthwise through the shaft and through or alongside of a portion of the first unit, the rod being off-set from the center axis of the shaft and being fixed at a distal end thereof to the second unit at a location removed from an axis of the second unit. A drive shaft is fixed to the rod at a proximal end of the rod, the drive shaft having a threaded portion and a non-threaded portion. The device further comprises actuator or operating means mounted on the base portion for (1) effecting rotational movement of the drive shaft and thereby rotational movement of the rod, with a consequent rotational movement of the second unit to a position removed from alignment with the first unit, and (2) effecting axial movement of the drive shaft and rod so as to effect axial movement of the second unit into position alongside the first unit.

In accordance with a further feature of the invention the device described herein above is an endoscope and at least one of the units comprises an electronic imaging sensor or video device.

The above and other features of the invention, including various novel details of construction and combinations of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of the invention, from which its novel features and advantages will be apparent.

In the drawings.

DESCRIPTION OF THE PREFERRED EMBODIMENTS

Figure 1:
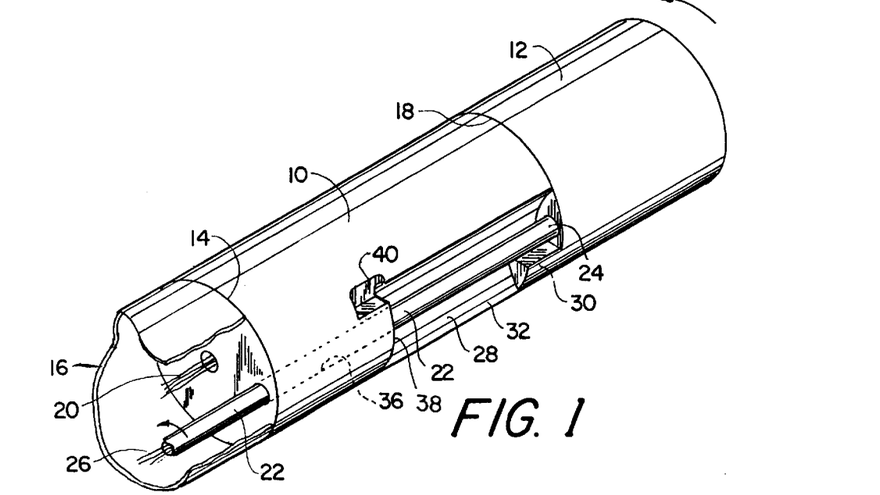
FIG. 1 is a perspective view of a pair of units mounted on a distal end of a shaft.

Referring to FIG. 1, it will be seen that in an illustrative embodiment of the invention there are provided first and second units 10, 12 mounted on a distal end 14 of a hollow shaft 16. The first unit 10 is fixed to the shaft 16 in end-to-end relationship, and is of the same outer configuration and size as the shaft 16, typically cylindrical. The second unit 12 is adapted to be positioned in alignment with the first unit 10 as shown in FIG. 1, and is further adapted to be moved transversely of the first unit 10 (FIG. 2) and axially of the first unit 10 (FIG. 3), as will be further described hereinbelow. The second unit 12, at least at its proximal end 18, preferably is of the same outer configuration and size as the first unit 10, such that the assembly of shaft 16, first unit 10, and second unit 12, in aligned relationship, as illustrated in FIG. 1, may be passed through a boundary layer, such as the skin of a mammal body or a vehicle subject to unusually harsh environments, requiring as small an orifice as possible.

In a preferred embodiment, the device illustrated in part in FIG. 1 comprises an endoscope in which the units 10, 12 are electronic imaging units, or capsules containing electronic imaging units. In such instances, electronic and fiber-optic leads, shown collectively at 20, may extend through the shaft 16 to the first unit 10 for the purpose of providing electrical connections to the electronic components of that imaging unit and transmitting light for illuminating the scene or site being viewed by the optical components of the imaging unit.

As used herein, the term "electronic imaging unit" comprises an electronic optical image sensor such as a CCD module and also one or more optical components for generating an optical image of the area under inspection and focusing that image onto the image sensor. Such a unit, also known in the art as a video camera or video device, may also comprise additional components for operating the image sensor and generating an electrical video output signal representative of the scene or site being inspected. By way of example but not limitation, for the purposes of this invention the electronic imaging units may be like the ones disclosed and illustrated by said U.S. Pat. Nos. 4,832,003, 5,021,888, 5,166,787, 5,662,584 and 5,538,497. The fiber optic leads may take the form of optical fibers or rods arranged in unit 10 for optimum transmission of light to illuminate the scene or site being inspected.

A stiff rod 22 extends through the shaft 16 and a bore 36 in first unit 10, and has its distal end 24 connected to the proximal end 18 of the second unit 12. Rod 22 extends parallel but eccentric to the longitudinal axis of shaft 16. Rod 22 is slidable lengthwise and is also rotatable on its own axis relative to shaft 16 and first unit 10. When the units 10, 12 comprise optical image sensors, or other electronic or electrical devices, or means for illuminating the scene or site under inspection, the rod 22 may be a tubular member having disposed therein additional electronic and/or fiber-optic leads, identified collectively by the numeral 26, that are connected to the second unit.

Figure 2:
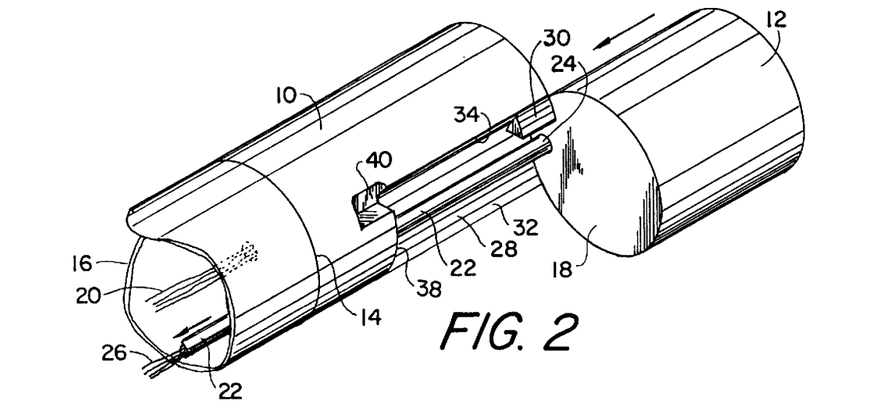
FIG. 2 is similar to FIG. 1, but shows one of the units moved rotatively out of alignment with the other of the units.

Referring to FIG. 2, it will be seen that rotation of the rod 22 on its axis causes corresponding rotative movement of the second unit 12 from the position shown in FIG. 1 to the position shown in FIG. 2. As noted above, the rod 22 is off-set from the axis of the shaft 16. Also rod 22 is joined to the second unit 12 at a location off-set from the axis of the second unit. Accordingly, rotation of the rod 22 causes lateral translational movement of the second unit 12 to a position no longer aligned with the first unit 10, as illustrated in FIG. 2.

The first unit 10 is provided with a groove 28 having a concave configuration complementary to the rounded configuration of the second unit 12, e.g., groove 28 has a circular curvature complementary to the circular curvature of the cylindrical outer surface of unit 12. The second unit 12 is provided with a detent 30 extending from the proximal end 18 of the second unit. Detent 30 extends parallel but is spaced radially from the center axis of second unit 12. When the second unit 12 is aligned with the first unit 10 (FIG. 1), the detent 30 extends into groove 28 and is engaged with a longitudinally-extending wall portion 32 of groove 28. On rotative movement of the second unit 12 (counterclockwise as seen in FIG. 1), the unit rotates until the detent 30 engages an opposite wall portion 34 of groove 28 (FIG. 2). Thus, the detent 30 serves as a stop member, stopping rotative movement of the second unit 12 in its fully aligned position (FIG. 1) and in its transversely fully extended position (FIG. 2).

Figure 3:
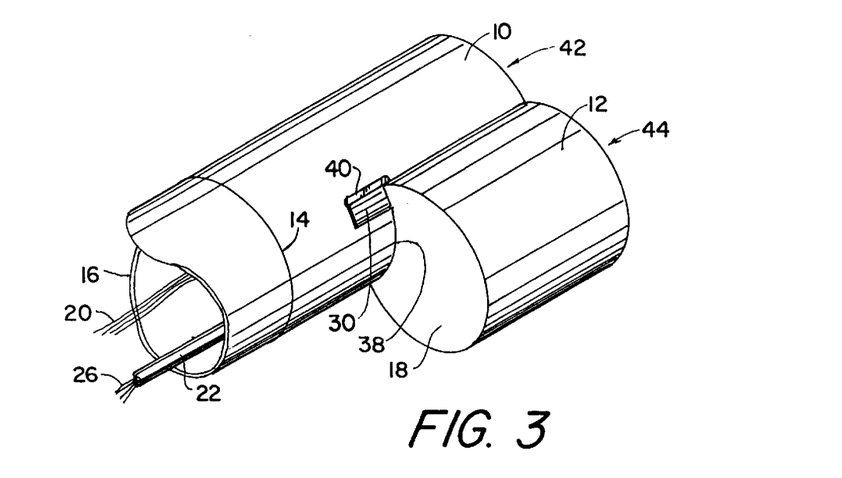
FIG. 3 is similar to FIG. 2, but shows the one unit moved axially to a position alongside the other unit.

As noted previously, rod 22 is movable axially and rotatable on its own axis in shaft 16 and bore 36 of the first unit 10. Accordingly, once the second unit 12 has been rotated to the position illustrated in FIG. 2, it may then be moved axially in a proximal direction (leftwardly, as viewed in FIG. 2) into and along the groove 28 to a proximal limit position shown in FIG. 3, wherein the proximal end 18 of the second unit 12 abuts a proximal end wall 38 of the groove 28. As the second unit's proximal end 18 approaches the groove end wall 38, the detent 30 enters a substantially complementary-shaped notch 40 in unit 10. When the unit 12 is in such position, the opposite edges of groove 28 lock the unit against rotation in either direction on the axis of rod 22. In this preferred embodiment, units 10, 12 are provided, respectively, with distal end faces 42, 44 (FIG. 3). Consequently, when the units 10, 12 are side-by-side as shown in FIG. 3, the faces 42, 44 lie in a common plane that intersects the longitudinal axis of shaft 16 at a right angle.

In a an contemplated embodiment in the form of an endoscope wherein both units 10, 12 are electronic optical imaging units, side-by-side positioning of the two imaging units provides stereoscopic viewing of an internal region of a mammal body. In a further contemplated embodiment wherein the units 10, 12 are acoustic sensing devices, such side-by-side positioning of the units provides for sound ranging determination by triangulation. It will be appreciated that for some applications it may be preferable for the units 10, 12 not to have their distal faces in a co-planar relationship, as, for example, where one unit is used to illuminate and/or observe surgical work or the like that is being done by means carried by or inserted through the other unit, in which case it may be preferable to have the illuminating and/or observing unit off-set rearwardly from the other unit.

Referring to FIG. 4–7, it will be seen that the illustrated instrument or device includes a base portion 50 to which a proximal end 46 of the shaft 16 is fixed. The base 50 may be shaped and sized to function as a handle whereby the device may be grasped and manipulated. The base portion 50 includes a base plate 52 to which is bolted a shaft mount 54 in which the proximal end of shaft 16 is rigidly secured. Also mounted to base portion 50 is an operating mechanism assembly or actuator assembly hereinafter described for imparting rotative and axial movement to the rod 22.

Figure 4:
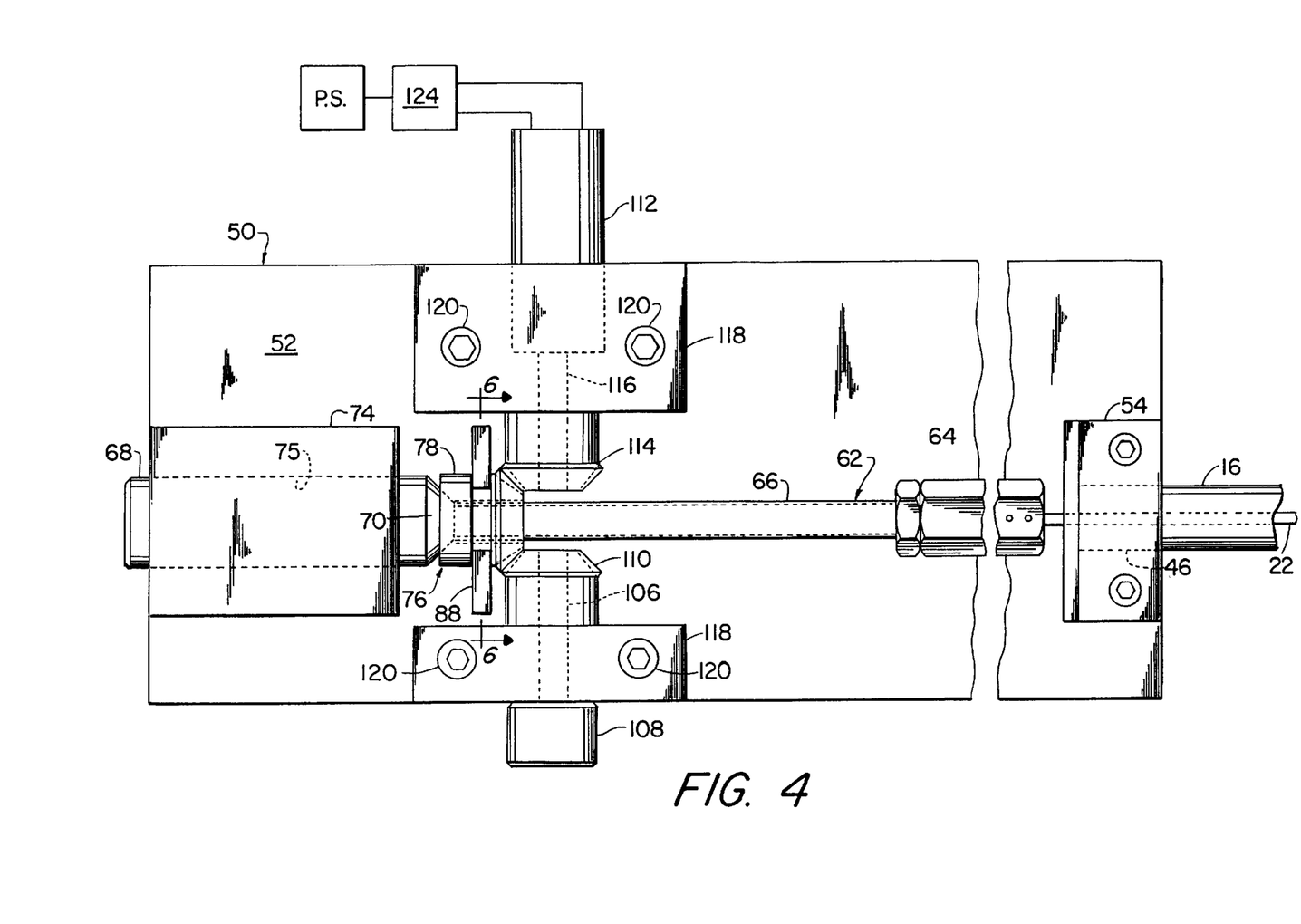
FIG. 4 is a top plan view, with portions broken away, of a base portion of the device.

The operating mechanism assembly comprises a drive shaft 62 that is connected by a coupling member 64 to the proximal end of rod 22. Shaft 62 comprises an externally threaded section 66 and a larger diameter unthreaded section 68. In the illustrated embodiment, the external screw thread on shaft section 66 is formed as a left hand thread. The distal or forward end of shaft portion 68 has a conically-shaped surface 70 that extends to the threaded section 66. The proximal portion 68 of shaft 62 is rotatably mounted in a vertical extension 74 of base plate 52. The latter has a bore 75 that is sized so as to make a close fit with shaft portion 68 such that the shaft is restrained against lateral movement while being free to slide axially and also to rotate on its own axis relative to the shaft mount portion 74.

Figure 8:
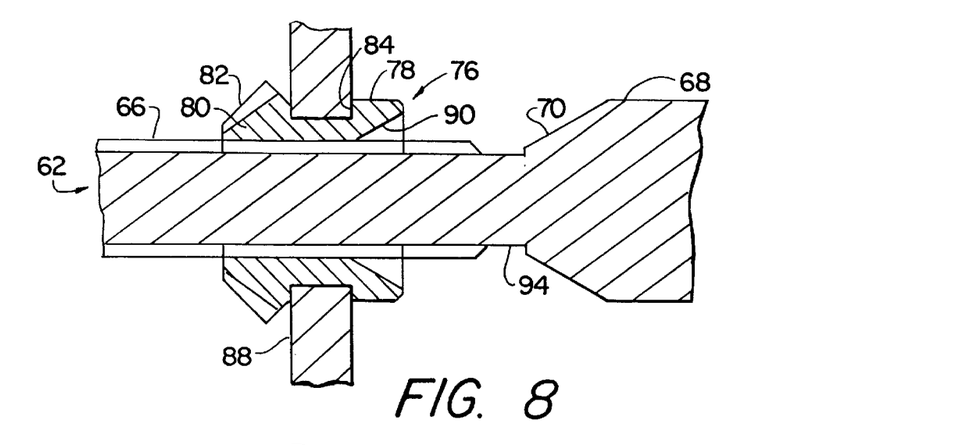
FIGS. 8 and 9 are longitudinal sectional view of portions of a gear nut, yoke and drive shaft shown in different relative operating positions.
Figure 9:
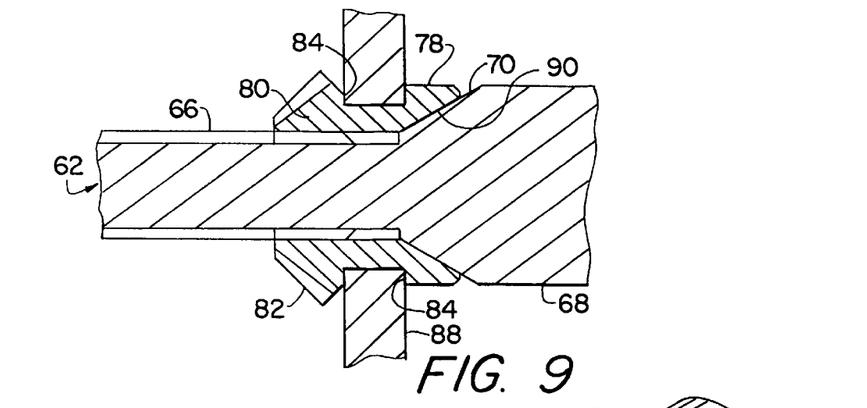

Rotatably mounted on the threaded portion 66 of shaft 62 is a gear nut 76. As seen in FIGS. 4, 8 and 9, gear nut 76 comprises a rear (proximal) portion 78 and a forward beveled gear portion 80 (FIGS. 8 and 9). The gear portion 80 is characterized by a circumferential array of gear teeth 82. Between the proximal portion 78 and the distal portion 80 of nut 76 is a groove 84. The latter is sized to make a close fitting connection with a yoke 88 that is attached to and extends vertically from base plate 52. The yoke functions to limit axial movement of nut 76 while allowing it to rotate. The internal surface of nut 76 is threaded with a left hand thread so as to mate with the external left hand threads on shaft 66. Additionally, at its proximal end the nut has a conical counterbore 90. The latter is sized so as to be able to make a tight contact with the conical outer surface 70 formed at the distal end of the rear portion 68 of shaft 62. Referring to FIGS. 8 and 9, it is preferred, but not essential, that the external threads on shaft 62 terminate short of the conical surface 70, leaving a portion 94 of shaft 62 unthreaded. The angle of the counterbore surface 90 is the same as the angle of the conical surface 70 on shaft 62, so that the two surfaces may make full engagement with one another when the nut shaft is rotated to bring its conical counterpart surface 90 into engagement with the conical shaft surface 70. When the two conical surfaces on shaft 62 and gear nut 76 are brought together they will tend to stick to one another due to friction, producing a self-locking action. This locking action can be enhanced by appropriately selecting the angles of the conical surfaces and the materials of which the shaft and gear nut are made (preferably steel), and by regulating the smoothness of the machined conical surfaces and the pitch of the screw threads. However, the two conical surfaces can be separated by applying a turning torque to the gear nut that is sufficient to break the frictional bond between surfaces 70 and 90.

The gear nut 76 and shaft 62, and specifically their conical surfaces 90 and 70 respectively, combine to form a friction clutch mechanism, the operation of which is described hereinafter.

Figure 5:
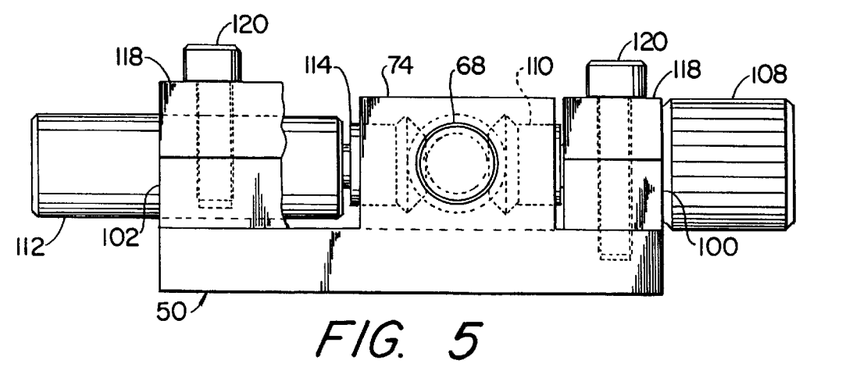
FIG. 5 is an end elevational view of the device of FIG. 4.
Figure 6:
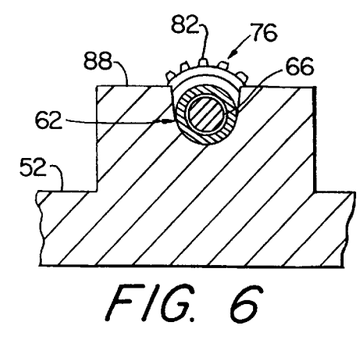
FIG. 6 is a fragmentary cross-sectional view taken along line 6—6 of FIG. 4.
Figure 7:
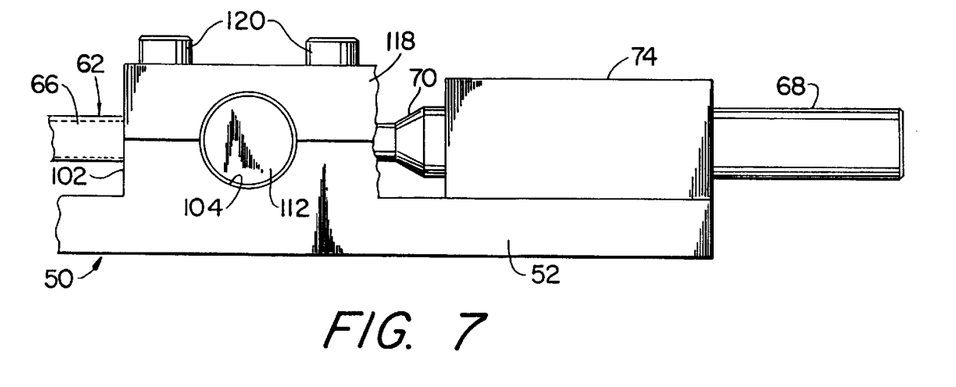
FIG. 7 is a side elevational view of the base portion of the device of FIG. 4.

Referring to FIGS. 4, 5 and 7, the base plate 52 has two vertically-extending rectangular posts or stanchions 100 and 102 that have circularly-shaped grooves 104 in their upper end surfaces. The groove 104 in post 100 serves as nesting place for a manually operable shaft 106 that has a large thumb wheel 108 at its outer end. The inner end of shaft 106 carries a bevel gear 110. The groove 104 in the other post 102 supports an electric motor 112 having another bevel gear 114 mounted on the end of its output shaft 116. Shaft 106 is rotatably held in place on post 100 by a clamp member 118 which is held in place by screw bolts 120. Similarly motor 112 is held in place on post 102 by another clamp member 118 which is held in place by additional screw bolts 120. The gears 110 and 114 are designed and positioned to mesh with gear 82. Shaft 106 is rotatable bidirectionally by hand, and motor 112 is a reversible motor so as to permit bidirectional rotation of its gear 114.

Motor 112 is adapted to be connected to a suitable power supply P.S. via switch means 124. The switch means are arranged and adapted to selectively energize the motor in a forward or reverse direction. The motor may be an a.c. motor or a d.c. motor. In the latter case the power supply may be a battery. It also is contemplated that a pneumatic or hydraulic motor may be used in place of an electric motor.

It should be noted that motor 112 and gear 14 may be omitted, in which case the device may be operated by rotating shaft 106 via thumb wheel 108. Alternatively shaft 106 may be omitted and the device operated by way of motor 112. If it is desired to have both operating means present, it is necessary to use a motor 112 whose operating shaft 116 is substantially free-wheeling when the motor is deenergized, so as keep low the amount of torque required to rotate shaft 106.

Operation of the foregoing apparatus will now be described, with movement of shaft 62 being affected by operation of motor 112. Assume that units 10 and 12, are aligned end-to-end (FIG. 1) for penetrating a boundary, via an aperture that is just large enough, or expandable enough, to permit entry of unit 12. By way of explanation, the boundary may be human tissue and the aperture may be an incision in that tissue 6. When the units 10, 12 are in this position, the gear nut's internal conical surface 90 is engaged with and frictionally locked to the external conical surface 70 of shaft 62. Motor 112 is energized in a forward direction, causing its gear 114 to turn gear nut 76 in a counter-clockwise direction as viewed in FIG. 6. However, gear nut 76 is frictionally locked tight on shaft 62 by virtue of being engaged with conical surface 70. Since unit 12 is not locked against rotation, gear nut 76 will not rotate on shaft 62, but instead gear nut 76 and shaft 62 will both rotate together, causing transverse movement of the second unit from the position shown in FIG. 1 to the position shown in FIG. 2. As described above, the second unit 12 is stopped in its transverse movement by engagement of the detent 30 with the groove wall portion 34. As a result, rod 22 and shaft 62 are thereupon prevented from further rotation. Further as a result, if motor 112 remains energized and continues to drive gear nut 76 in the same direction, the gear nut will break its frictional bond with the shaft's conical surface 70 and continue to rotate under the driving force exerted by the motor. This continued rotation of the gear nut 76 on shaft 62 causes the latter to move axially and rearwardly in support 72 until the second unit 12 is drawn alongside the first unit (FIG. 3), at which point the motor 112 will tend to stall and may be shut off automatically by a current-sensing limit switch (not shown), or manually by the surgeon, to avoid motor overheating.

When it is desired to return the second unit 12 to a position in line with the first unit 10, the motor 112 is activated in a reverse direction, rotating the gear nut 76 in a clockwise duration. This reverse rotation of gear nut 76 causes shaft 62 to move axially from the position shown in FIG. 3 to the position shown in FIG. 2. At substantially the same time as the second unit proximal end 18 clears the first unit 10, the internal conical surface 90 of the gear nut engages conical surface 70 of shaft 62, stopping axial movement of the screw shaft and locking the gear nut to the shaft by virtue of a frictional bond being established between the mutually engaged surfaces 70 and 90. As a result, further rotation of the gear nut in the same clockwise direction causes the second unit 12 to rotate from the position shown in FIG. 2 to the position shown in FIG. 1, at which time the motor 112 will tend to stall and may be shut off automatically by the same or a different current-sensing limit switch, or manually by the surgeon, to avoid motor overheating.

The operation of the device by grasping and rotating thumb wheel 108 is substantially identical to the above-described operation of the device using motor 112. When both operating mechanisms are present, the manual one serves as a back-up for the motorized one.

Although not shown, it is contemplated that a cover member may be provided for attachment to base plate 52, with the cover member being shaped so as to conceal the operating mechanism without interfering with its performance. That cover member and base portion 50 would form a housing that also serves as a handle by which the entire unit may be held.

Figure 10:
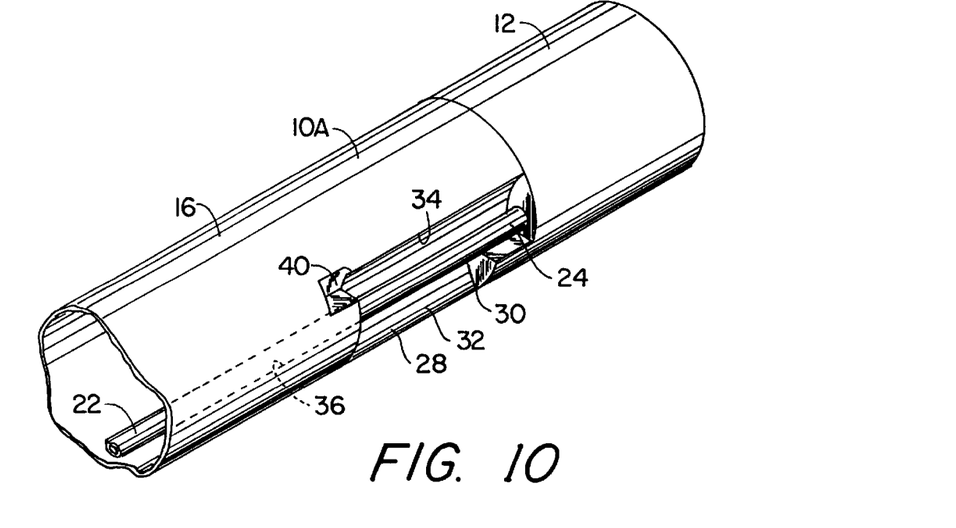
FIG. 10 is a view similar to FIG. 1 of an alternative embodiment of the device.

Referring now to FIG. 10, it is contemplated that instead of being a discrete unit affixed to the shaft 16, as described above, the unit 10 may comprise a hollow end portion 10A of the shaft 16. In the latter case, the first unit contained by the end portion 10a may be a discrete video unit comprising an electronic image sensor, an optical system (comprising at least an objective lens) for focusing an image of a scene or site being viewed onto the image sensor, and illuminating means for illuminating the scene or site. Alternatively, the end portion 10A may serve simply as a conduit for introducing a surgical instrument to the surgical site, while the video unit 12 serves as a means for observing the surgical site. It also is contemplated that the end portion 10A may serve as a housing for an electronic acoustic energy-sensing unit.

It is to be understood that the present invention is by no means limited to the particular construction or modification herein disclosed and/or shown in the drawings, but may comprise other modifications or equivalents within the scope of the claims. For example, for some applications, the outer configuration and size of the first unit 10 may be different than that of shaft 16, and the second unit 12 need not have the same size and configuration as first unit 10 or shaft 16. It also is contemplated that shaft 16 and rod 22 may be flexible instead of rigid or stiff. The manually operated shaft 106 may be modified so as to be driven by a second motor. Another contemplated modification is to mount the motor 112 so that its output shaft 116 extends parallel rather than at a right angle to drive shaft 62, and then appropriately modify the gearing that couples motor shaft 116 to gear portion 80 of nut 66. A further possible modification is to use gears that are not beveled. It also is contemplated to modify the gear teeth on nut 76 so as to permit using a sprocket and timing belt arrangement for coupling motor shaft 116 and/or shaft 106 to that nut. Also instead of having the gear teeth 82 on nut 76, a portion of the exterior of the nut could be shaped so as to function as a friction roller, and the shafts 106 and 116 could be fitted with friction rollers in place of gears, with the friction rollers on shafts 106 and 116 engaging the corresponding portion on the nut to effect rotation of the nut. Another possible modification is to replace the specific form of friction clutch mechanism shown in the drawings with a different form of clutch mechanism.

Still other modifications will be obvious to persons skilled in the art.

Having thus described my invention, what we claim as new and desire to secure by Letters Patent of the United States is:

1. A device for carrying first and second units in aligned end-to-end disposition at a distal end of a shaft and for moving said second unit into a predetermined position alongside said first unit, said device comprising:

a shaft having proximal and distal ends; first and second units adapted to be aligned in end-to-end disposition; a base portion to which the proximal end of said shaft is fixed, said first unit being fixed to the distal end of said shaft in alignment with said shaft;

a rod extending lengthwise through said shaft and through a portion of said first unit, said rod being off-set from an axis of said shaft and being fixed at a distal end thereof to said second unit at a location removed from an axis of said second unit;

a drive shaft fixed to said rod at a proximal end of said rod, said drive shaft having a threaded portion and a non-threaded portion; and an operating mechanism mounted on said base portion for sequentially (a) effecting rotational movement of said drive shaft to effect rotational movement of said rod in a direction to thereby rotate said second unit from said aligned end-to-end disposition to a position removed from alignment with said first unit, and (b) effecting axial movement of said drive shaft and said rod in a direction to move said second unit into said predetermined position alongside said first unit, said operating mechanism comprising a gear friction clutch that is engaged when said first and second units are in end-to-end disposition and disengaged while said drive shaft and said rod are being rotated and undergoing axial movement.

2. The device according to claim 1 wherein said gear friction clutch comprises a gear nut screwed onto said threaded portion of said drive shaft and adapted for frictionally clutching said non-threaded portion of said shaft when said nut is rotated in a predetermined direction relative to said shaft, and drive means mounted to said base portion for rotating said gear nut.

3. The device according to claim 2 wherein said drive means includes a drive gear that is engaged with said gear nut so that rotation of said drive gear will cause rotation of said gear nut.

4. The device in accordance with claim 3 wherein said drive gear is mounted on an actuating shaft having grip means for manual turning said actuating shaft.

5. The device in accordance with claim 3 wherein said drive gear is mounted on the output shaft of a reversible electrical motor, whereby energization of said motor will cause said drive gear to rotate said gear nut.

6. The device in accordance with claim 2 wherein said gear nut is restrained against movement lengthwise of said drive shaft.

7. The device in accordance with claim 6 wherein said gear nut has a circumferentially-extending peripheral groove, and further including means attached to said base portion and extending into said groove for restraining said gear nut against movement lengthwise of said drive shaft.

8. The device in accordance with claim 6 wherein said gear nut has an internal conically shaped clutch surface and said non-threaded portion of said drive shaft has an external conically shaped clutch surface adapted to make a friction tight engagement with said internal conically shaped clutch surface when said gear nut is rotated in a first direction relative to said drive shaft, whereby further rotational movement of said gear nut will result in rotational movement of said drive shaft in the same direction.

9. The device in accordance with claim 1 wherein said first unit is provided with a concave groove in a circular periphery thereof, and said rod extends lengthwise of said first unit in said groove, said groove having a curvature substantially equal to the curvature of said second unit, said groove being thereby configured to receive said second unit as said second unit is drawn axially into said groove by said rod to be placed in said position alongside said first unit.

10. The device in accordance with claim 9 wherein said first unit is provided with a notch extending from said groove, and said second unit is provided with a detent configured to be snugly received by said notch when said second unit is in said position alongside said first unit to prevent rotative movement of said second unit in said position.

11. The device in accordance with claim 10 wherein said detent extends from an end of said second unit and is adapted to extend into said groove of said first unit and serves as a stop member to limit rotative movement of said second unit relative to said first unit.

12. The device in accordance with claim 10 wherein said base portion includes a handle component.

13. An observation device comprising:
a shaft having a proximal and a distal end;
first and second discrete observation units, with said first observation unit fixed to said distal end of said shaft in alignment with said shaft;
a rod having a proximal end and a distal end, said rod extending lengthwise through said shaft and through a portion of said first unit, said rod being off-set from an axis of said shaft and being fixed at said distal end thereof to said second unit at a location offset from the center axis of said second unit; and
operating means for moving said second unit between a first position in which it is aligned end-to-end with said first unit and a second position in which said second unit is disposed alongside of and parallel to said first unit, said operating means comprising means for sequentially effecting (a) rotational movement of said rod in a first rotational direction to effect rotational movement of said second unit relative to said first unit, and (b) axial movement of said rod to effect axial movement of said second unit in a first axial direction relative to said first unit, said operating means also being adapted to move said second unit from said second position back to said first position by sequentially effecting (a) axial movement of said rod to effect axial movement of said second unit in a second axial direction relative to said first unit and (b) rotational movement of said rod in a second rotational direction to effect rotational movement of said second unit relative to said first unit.

14. The device in accordance with claim 13 further including a base portion and wherein said operating means comprises an extension of said rod having an externally threaded portion and an external conically shaped surface, a drive gear, means attached to said base portion for rotatably supporting said drive gear, a yoke fixed to said base portion, an internally threaded nut mounted on and connected to said externally threaded portion by a screw connection, said nut having a first gear portion engaged with said drive gear, a second holding portion engaged with said yoke whereby said nut is restrained against axial movement by said while remaining free to rotate on said externally threaded portion of said rod extension, and a third conical portion which is adapted to engage said external conically shaped surface of said rod extension whereby to rotative movement of said nut relative to said rod extension and thereby terminate axial movement of said rod extension by relative rotation of said rod extension and said nut.

15. The device in accordance with claim 14 further including manually operable means for effecting rotation of said drive gear.

16. The device in accordance with claim 14 further including a bidirectional electrical motor coupled to said drive gear for effecting rotation of said drive gear and thereby effecting rotational and axial movement of said rod extension and said rod.

17. The device in accordance with claim 13 wherein said first unit is provided with a concave groove in a circular periphery thereof, and said rod extends lengthwise of said first unit in said groove, said groove having a curvature substantially equal to the curvature of said second unit, said groove being thereby configured to receive said second unit as said second unit is drawn axially into said groove by said rod to be placed in said position alongside said first unit.

18. The device in accordance with claim 14 wherein said base portion includes a handle component.

19. The device in accordance with claim 13 wherein said first unit is provided with a notch extending from said groove, and said second unit is provided with a detent configured to be snugly received by said notch when said second unit is in said position alongside said first unit to prevent rotative movement of said second unit in said position.

20. The device in accordance with claim 19 wherein said detent extends from an end of said second unit and is adapted to extend into said groove of said first unit and serves as a stop member to limit rotative movement of said second unit relative to said first unit.

21. The device in accordance with claim 13 wherein said device comprises an endoscope and at least one of said first and second units comprises an electronic optical image sensor.

22. A device for carrying first and second units in tandem and moving the second of said units to a position abreast of the first of said units, said device comprising:
first and second units;
a base portion, said first unit being fixed to said base portion;
a rod extending through said first unit removed from an axis of said first unit and connected to said second unit at a point removed from an axis of said second unit,
said rod being fixed to a screw member having a threaded portion and a non-threaded portion;
said non-threaded portion of said screw member being disposed in a bore in a frame member mounted on said base portion, and having a conical portion proximate said screw member threaded portion;
a nut threadably mounted on said screw member and having a rotary gear portion, and internal conical portion complementary to and in alignment with said non-threaded screw conical portion, and a holding portion by which said nut is retained by a yoke fixed to said base portion, said nut being limited by said yoke to only rotational movement;

a rotary drive gear mounted on said base portion and threadedly engaged with said nut rotary gear portion; and an actuator mounted on said base portion and connected to said rotary drive gear for effecting rotation of said rotary drive gear;

whereby upon rotation of said actuator, said rotary drive gear turns said nut, said conical portion of said nut being frictionally engaged with said conical surface of said screw member, such that turning said nut causes turning of said screw member, to cause turning of said rod to move said second unit transversely to said first unit to a position out of alignment with said first unit, and whereby upon said second unit reaching the end of its transverse movement, rotation of said screw member is stopped and continued turning of said rotary drive gear causes continued turning of said nut rotary gear portion to move said screw member axially, thereby to move said rod axially, to move said second unit axially to said position abreast of said first unit; and to move said screw member conical surface away from said nut conical portion; and whereby upon counter rotation of said actuator and said rotary drive gear, said nut gear portion turns and moves said screw member and said rod and said second unit axially until a rearward surface of said second unit clears a forward surface of said first unit substantially at which time said screw member conical surface engages said nut conical portion to prevent further axial movement of said screw member in said nut, and to frictionally fix said screw member to said nut, and further rotation of said nut causes rotation of said screw member and said rod, to return said second unit to said position in tandem with said first unit.

* * * * *

UNITED STATES PATENT AND TRADEMARK OFFICE
CERTIFICATE OF CORRECTION

PATENT NO. : 5,935,057
DATED : August 10, 1999
INVENTOR(S) : Philip R. Lichtman et al It is certified that error appears in the above-indentified patent and that said Letters Patent is hereby corrected as shown below:

Claim 1, column 8, line 17, the words "first and second..." should start a new paragraph;

Claim 1, column 8, lines 18 and 19, the words "a base portion..." should start a new paragraph;

Claim 4, column 8, line 57, the word "manual" should be changed to -- manually --;

Claim 14, column 10, line 8, delete the words "by said";

Claim 14, column 10, line 12, insert the word "stop" before the word -- rotative --.

Signed and Sealed this

Eighth Day of February, 2000

Attest:

Q. TODD DICKINSON

*Attesting Officer*  *Commissioner of Patents and Trademarks*